US012564653B2

(12) United States Patent
Kim et al.

(10) Patent No.: US 12,564,653 B2
(45) Date of Patent: Mar. 3, 2026

(54) DEODORIZATION MODULE AND ELECTRONIC DEVICE COMPRISING SAME

(71) Applicant: SEOUL VIOSYS CO., LTD., Ansan-si (KR)

(72) Inventors: Ji Won Kim, Ansan-si (KR); Jae Hak Jeong, Ansan-si (KR); Byeong Cheol Ju, Ansan-si (KR); Sang Cheol Shin, Ansan-si (KR)

(73) Assignee: SEOUL VIOSYS CO., LTD., Ansan-si (KR)

( * ) Notice: Subject to any disclaimer, the term of this patent is extended or adjusted under 35 U.S.C. 154(b) by 219 days.

(21) Appl. No.: 17/897,888

(22) Filed: Aug. 29, 2022

(65) Prior Publication Data

US 2022/0401612 A1 Dec. 22, 2022

Related U.S. Application Data

(63) Continuation of application No. 16/607,432, filed as application No. PCT/KR2018/004135 on Apr. 9, 2018, now Pat. No. 11,452,792.

(30) Foreign Application Priority Data

Apr. 25, 2017 (KR) ........................ 10-2017-0053086

(51) Int. Cl.
*A61L 9/20* (2006.01)
*A61L 9/22* (2006.01)

(52) U.S. Cl.
CPC ................ *A61L 9/205* (2013.01); *A61L 9/22* (2013.01); *A61L 2209/12* (2013.01); *A61L 2209/14* (2013.01); *A61L 2209/15* (2013.01)

(58) Field of Classification Search
CPC ... A61L 9/20; A61L 9/205; A61L 9/22; A61L 2209/12; A61L 2209/14
See application file for complete search history.

(56) References Cited

U.S. PATENT DOCUMENTS

| | | | | |
|---|---|---|---|---|
| 2006/0177356 A1* | 8/2006 | Miller | ....................... | A61L 9/20 |
| | | | | 422/121 |
| 2008/0170971 A1* | 7/2008 | Bergeron | .................. | A61L 9/22 |
| | | | | 422/186.04 |
| 2016/0051719 A1 | 2/2016 | Watanabe et al. | | |
| 2019/0083674 A1 | 3/2019 | Jeong et al. | | |

FOREIGN PATENT DOCUMENTS

| | | |
|---|---|---|
| CN | 1734190 | 2/2006 |
| CN | 201123912 | 10/2008 |

(Continued)

OTHER PUBLICATIONS

JP Office Action for JP Application No. 2019-557805 issued on Feb. 8, 2022 (with English Translation).

(Continued)

*Primary Examiner* — Timothy C Cleveland
(74) *Attorney, Agent, or Firm* — Perkins Coie LLP

(57) ABSTRACT

A deodorization module including a housing having a suction port and a discharge port formed therein, a fan disposed between the suction port and the discharge port, a photocatalytic filter disposed between the suction port and the fan, a light source module including a substrate and an ultraviolet light source and configured to irradiate the photocatalytic filter with ultraviolet light, and an ion generator disposed between the fan and the discharge port.

19 Claims, 15 Drawing Sheets

(56) References Cited

FOREIGN PATENT DOCUMENTS

| CN | 202136607 | 2/2012 |
| CN | 203274062 | 11/2013 |
| JP | 2001-029778 | 2/2001 |
| JP | 3112295 | 8/2005 |
| JP | 2009195665 | 9/2009 |
| JP | 3157326 | 2/2010 |
| JP | 2016048683 A | 4/2016 |
| KR | 10-2003-0072095 | 9/2003 |
| KR | 20070087819 A | 8/2007 |
| KR | 10-2016-0015084 | 2/2016 |
| KR | 10-2016-0068075 | 6/2016 |

OTHER PUBLICATIONS

CN Office Action for CN Application No. 201880005014.9 issued on Dec. 23, 2021 (with English Translation).

International Search Report mailed Jul. 13, 2018, in International Application No. PCT/KR2018/004135 (with English Translation).
Second Chinese Office Action issued Apr. 8, 2021, issued in Chinese Application No. 201880005014.9 (with English Translation).
Yunxian Yao et al., "Indoor Environmental Pollution Control", China Environmental Science Publishing House, 2007.6, pp. 93-95 (with English Translation).
Chinese Office Action dated Aug. 14, 2020 issued in Chinese Patent Application No. 201880005014.9.
KalYan Chen, Ventilation Engineering, Journal, Nov. 1, 2003, pp. 1-4, China Mining University Press.
Jun Zhang, Automobile Body Electrical and Auxiliary Electrical Equipment, Journal, Jan. 1, 2013, pp. 1-5, Yellow River Water Conservancy Press.
Section 6 Automatic Control and Regulation of Automobile Air Conditioning, Journal, pp. 1-2.
English Translation of Office Action from corresponding Japan Patent Application No. 2019-557805, dated Mar. 28, 2023 (5 pages).

* cited by examiner

DEODORIZATION MODULE AND ELECTRONIC DEVICE COMPRISING SAME

CROSS-REFERENCE TO RELATED APPLICATIONS

This application is a continuation of U.S. application Ser. No. 16/607,432, filed on Jan. 20, 2020, which is a National Stage Entry of International Patent Application No. PCT/KR2018/004135, filed on Apr. 9, 2018, and claims priority from and the benefit of Korean Patent Application No. 10-2017-0053086, filed on Apr. 25, 2017, each of which are incorporated by reference for all purposes as if fully set forth herein.

BACKGROUND

Field

Exemplary embodiments of the present invention relate to a deodorization module and an electronic device including the same.

Discussion of the Background

In refrigerators, furniture, vehicles, and indoors, unpleasant odors are generated by various toxic substances. For example, the refrigerator produces unpleasant odors due to decay of food, and furniture and vehicle interiors produce unpleasant odors due to poor ventilation. Moreover, volatile organic compounds emitted from materials of the furniture, vehicles, interiors, and the like often produce unpleasant odors.

In order to remove such unpleasant odors, various types of deodorization modules, such as a filter type, an ion and ozone generation type, and a UV irradiation type, are used in the art.

Generally, a deodorization module is configured to perform deodorization through one of the various deodorization types. However, the deodorization module adopting one deodorization type has a problem of insufficient deodorization of air upon intake of a large amount of air.

The above information disclosed in this Background section is only for understanding of the background of the inventive concepts, and, therefore, it may contain information that does not constitute prior art.

SUMMARY

Exemplary embodiments of the present invention provide a deodorization module capable of deodorizing air.

Exemplary embodiments also provide a deodorization module using ions and a photocatalyst.

Exemplary embodiments further provide a deodorization module capable of achieving sufficient deodorization even upon intake of large amount of air.

Exemplary embodiments also provide a deodorization module including components arranged and configured to improve deodorization efficiency.

A deodorization module according to an exemplary embodiment includes a housing having a suction port and a discharge port, a fan disposed between the suction port and the discharge port, a photocatalyst filter disposed between the suction port and the fan, a light source module including a substrate and a UV light source and configured to emit UV light towards the photocatalyst filter, and an ion generator disposed between the fan and the discharge port.

The deodorization module may employ both ions and a photocatalyst to improve deodorization efficiency.

The deodorization module can achieve sufficient deodorization through double deodorization of air, even upon intake of a large amount of air.

The deodorization module allows photocatalytic reaction and chemical reaction between ions and organic compounds to occur under optimal conditions through suitable arrangement and structures of components therein.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate exemplary embodiments of the invention, and together with the description serve to explain the inventive concepts.

DETAILED DESCRIPTION

Figure 1:
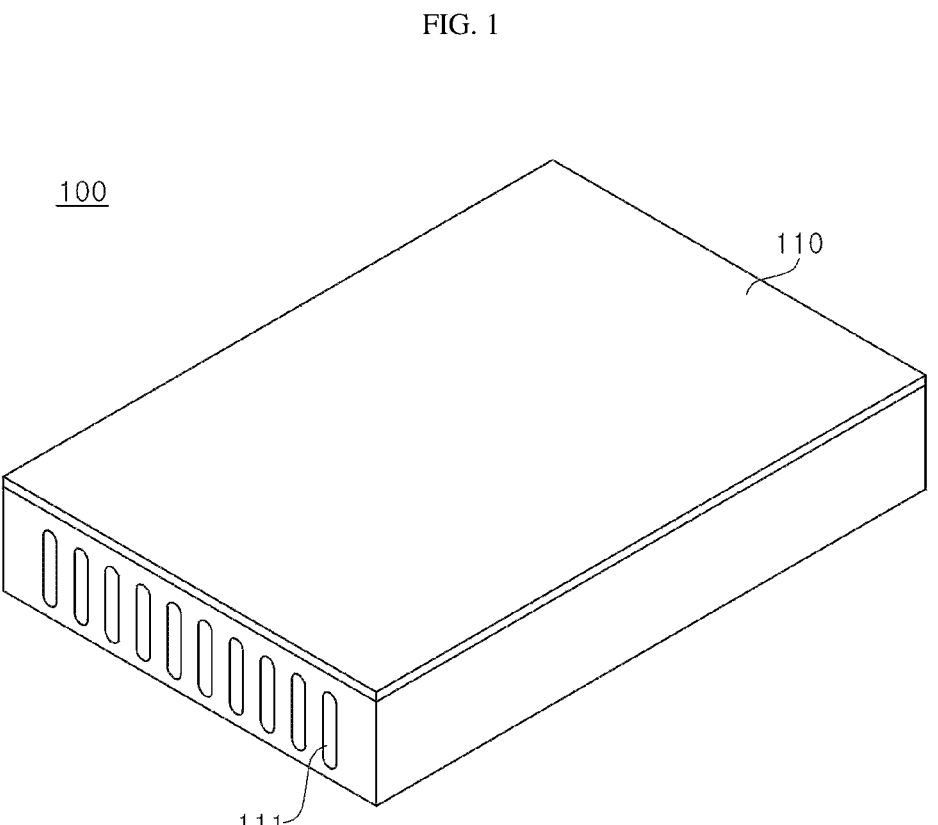
FIGS. 1, 2, 3, and 4 are exemplary views of a deodorization module according to a first exemplary embodiment.

In the following description, for the purposes of explanation, numerous specific details are set forth in order to provide a thorough understanding of various exemplary embodiments or implementations of the invention. As used herein "embodiments" and "implementations" are interchangeable words that are non-limiting examples of devices or methods employing one or more of the inventive concepts disclosed herein. It is apparent, however, that various exemplary embodiments may be practiced without these specific details or with one or more equivalent arrangements. In other instances, well-known structures and devices are shown in block diagram form in order to avoid unnecessarily obscuring various exemplary embodiments. Further, various exemplary embodiments may be different, but do not have to be exclusive. For example, specific shapes, configurations, and characteristics of an exemplary embodiment may be used or implemented in another exemplary embodiment without departing from the inventive concepts.

Unless otherwise specified, the illustrated exemplary embodiments are to be understood as providing exemplary features of varying detail of some ways in which the inventive concepts may be implemented in practice. Therefore, unless otherwise specified, the features, components, modules, layers, films, panels, regions, and/or aspects, etc. (hereinafter individually or collectively referred to as "elements"), of the various embodiments may be otherwise combined, separated, interchanged, and/or rearranged without departing from the inventive concepts.

The use of cross-hatching and/or shading in the accompanying drawings is generally provided to clarify boundaries between adjacent elements. As such, neither the presence nor the absence of cross-hatching or shading conveys or indicates any preference or requirement for particular materials, material properties, dimensions, proportions, commonalities between illustrated elements, and/or any other characteristic, attribute, property, etc., of the elements, unless specified. Further, in the accompanying drawings, the size and relative sizes of elements may be exaggerated for clarity and/or descriptive purposes. When an exemplary embodiment may be implemented differently, a specific process order may be performed differently from the described order. For example, two consecutively described processes may be performed substantially at the same time or performed in an order opposite to the described order. Also, like reference numerals denote like elements.

When an element, such as a layer, is referred to as being "on," "connected to," or "coupled to" another element or layer, it may be directly on, connected to, or coupled to the other element or layer or intervening elements or layers may be present. When, however, an element or layer is referred to as being "directly on," "directly connected to," or "directly coupled to" another element or layer, there are no intervening elements or layers present. To this end, the term "connected" may refer to physical, electrical, and/or fluid connection, with or without intervening elements. Further, the D1-axis, the D2-axis, and the D3-axis are not limited to three axes of a rectangular coordinate system, such as the x, y, and z-axes, and may be interpreted in a broader sense. For example, the D1-axis, the D2-axis, and the D3-axis may be perpendicular to one another, or may represent different directions that are not perpendicular to one another. For the purposes of this disclosure, "at least one of X, Y, and Z" and "at least one selected from the group consisting of X, Y, and Z" may be construed as X only, Y only, Z only, or any combination of two or more of X, Y, and Z, such as, for instance, XYZ, XYY, YZ, and ZZ. As used herein, the term "and/or" includes any and all combinations of one or more of the associated listed items.

Although the terms "first," "second," etc. may be used herein to describe various types of elements, these elements should not be limited by these terms. These terms are used to distinguish one element from another element. Thus, a first element discussed below could be termed a second element without departing from the teachings of the disclosure.

Spatially relative terms, such as "beneath," "below," "under," "lower," "above," "upper," "over," "higher," "side" (e.g., as in "sidewall"), and the like, may be used herein for descriptive purposes, and, thereby, to describe one elements relationship to another element(s) as illustrated in the drawings. Spatially relative terms are intended to encompass different orientations of an apparatus in use, operation, and/or manufacture in addition to the orientation depicted in the drawings. For example, if the apparatus in the drawings is turned over, elements described as "below" or "beneath" other elements or features would then be oriented "above" the other elements or features. Thus, the exemplary term "below" can encompass both an orientation of above and below. Furthermore, the apparatus may be otherwise oriented (e.g., rotated 90 degrees or at other orientations), and, as such, the spatially relative descriptors used herein interpreted accordingly.

The terminology used herein is for the purpose of describing particular embodiments and is not intended to be limiting. As used herein, the singular forms, "a," "an," and "the" are intended to include the plural forms as well, unless the context clearly indicates otherwise. Moreover, the terms "comprises," "comprising," "includes," and/or "including," when used in this specification, specify the presence of stated features, integers, steps, operations, elements, components, and/or groups thereof, but do not preclude the presence or addition of one or more other features, integers, steps, operations, elements, components, and/or groups thereof. It is also noted that, as used herein, the terms "substantially," "about," and other similar terms, are used as terms of approximation and not as terms of degree, and, as such, are utilized to account for inherent deviations in measured, calculated, and/or provided values that would be recognized by one of ordinary skill in the art.

Various exemplary embodiments are described herein with reference to sectional and/or exploded illustrations that are schematic illustrations of idealized exemplary embodiments and/or intermediate structures. As such, variations from the shapes of the illustrations as a result, for example, of manufacturing techniques and/or tolerances, are to be expected. Thus, exemplary embodiments disclosed herein should not necessarily be construed as limited to the particular illustrated shapes of regions, but are to include deviations in shapes that result from, for instance, manufacturing. In this manner, regions illustrated in the drawings may be schematic in nature and the shapes of these regions may not reflect actual shapes of regions of a device and, as such, are not necessarily intended to be limiting.

Unless otherwise defined, all terms (including technical and scientific terms) used herein have the same meaning as commonly understood by one of ordinary skill in the art to which this disclosure is a part. Terms, such as those defined in commonly used dictionaries, should be interpreted as having a meaning that is consistent with their meaning in the context of the relevant art and should not be interpreted in an idealized or overly formal sense, unless expressly so defined herein.

A deodorization module according to an exemplary embodiment includes a housing having a suction port and a discharge port, a fan disposed between the suction port and the discharge port, a photocatalyst filter disposed between the suction port and the fan, a light source module including a substrate and a UV light source and configured to emit UV light towards the photocatalyst filter, and an ion generator disposed between the fan and the discharge port.

The photocatalyst filter may be disposed on one side of the housing, and the light source module may be disposed on the other side of the housing.

The photocatalyst filter may include a first filter disposed on one side of the housing and a second filter disposed on the other side of the housing, and the light source module may be disposed between the first and second filters. The light source module may include UV light sources mounted on both surfaces of the substrate. Further, the deodorization module may include two light source modules each including the UV light source mounted on one surface of the substrate. One of the light source modules may emit UV light towards the first filter, and the other light source module may emit UV light towards the second filter. The two light source modules may be separated from each other. In addition, the photocatalyst filter may be disposed on a ceiling surface of the housing, and the light source module may be disposed on a bottom surface of the housing.

Alternatively, the photocatalyst filter may be disposed on the bottom surface of the housing, and the light source module may be disposed on the ceiling surface of the housing.

Alternatively, the photocatalyst filter may be disposed on each of the ceiling and bottom surfaces of the housing, and the light source module may be disposed between the first and second filters.

Alternatively, the light source module may be disposed on each of one side and the other side of the housing. The photocatalyst filter may be disposed between the light source modules. In addition, the light source module may include UV light sources mounted on both surfaces of the substrate, respectively. Further, the deodorization module may include two light source modules each including the UV light source mounted on one surface of the substrate. One of the light source modules may emit UV light towards the photocatalyst filter disposed on the ceiling surface of the housing, and the other light source module is disposed to emit UV light towards the photocatalyst filter disposed on the bottom surface of the housing. The two light source modules may be separated from each other.

In addition, the light source modules may be disposed on the ceiling and bottom surfaces of the housing, respectively, and the photocatalyst filter may be disposed between the light source modules.

The deodorization module may further include a flow channel guide formed between the fan and the ion generator, in which the flow channel guide may have one side adjoining the bottom surface of the housing and the other side adjoining an upper end of one side of the ion generator. An upper surface of the flow channel guide may be a slanted flat surface or a downwardly concave surface.

The housing may further include a securing portion configured to secure the fan, and the securing portion may be formed to receive both sides of the fan.

The housing may further include a first inner wall extending from opposite sides of the securing portion towards one side and the other side of the housing. An upper surface of the first inner wall may adjoin the ceiling surface of the housing and a lower surface of the first inner wall may adjoin the bottom surface of the housing.

The housing may further include a second inner wall extending from one side and the other side of the housing to adjoin opposite sides of the ion generator. The second inner wall may have a height equal to or less than that of the ion generator. Alternatively, the second inner wall may have a greater height than that of the ion generator.

A distance between the light source module and the photocatalyst filter may be greater than a distance between the light source module and the fan. More specifically, the distance between the light source module and the photocatalyst filter may be 0.5 times or more the distance between the light source module and the fan.

The housing may further include a light source module securing portion configured to secure the light source module.

The light source module securing portion includes a first light source module securing portion including an insertion portion formed to receive opposite sides of the light source module.

The first light source module securing portion may further include a support portion disposed under the insertion portion to support the insertion portion.

The light source module securing portion may further include a second light source module securing portion protruding upwards from the bottom surface of the housing to contact an upper side surface of the light source module.

The housing may further include a photocatalyst module securing portion configured to secure the photocatalyst module. The photocatalyst module securing portion may receive opposite sides of the photocatalyst module. Alternatively, the photocatalyst module securing portion may be formed between the photocatalyst module securing portion and the suction port, and be separated from the suction port of the housing.

FIG. 1 to FIG. 4 are exemplary views of a deodorization module according to a first exemplary embodiment.

Figure 2:
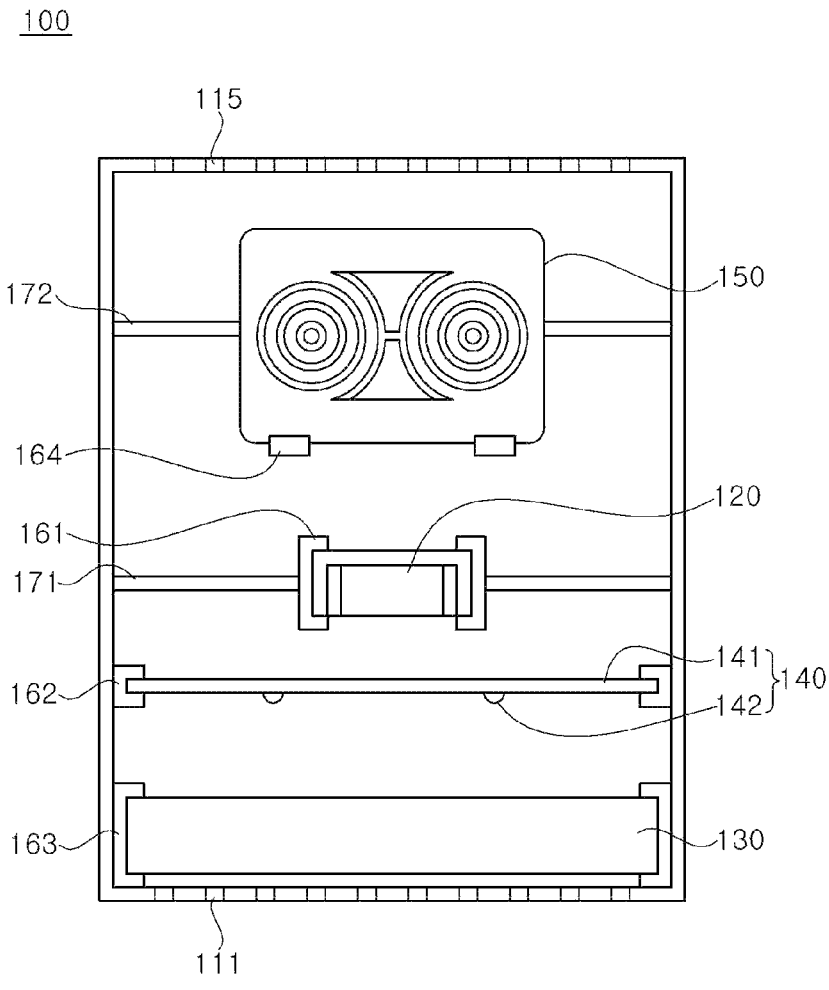
Figure 3:
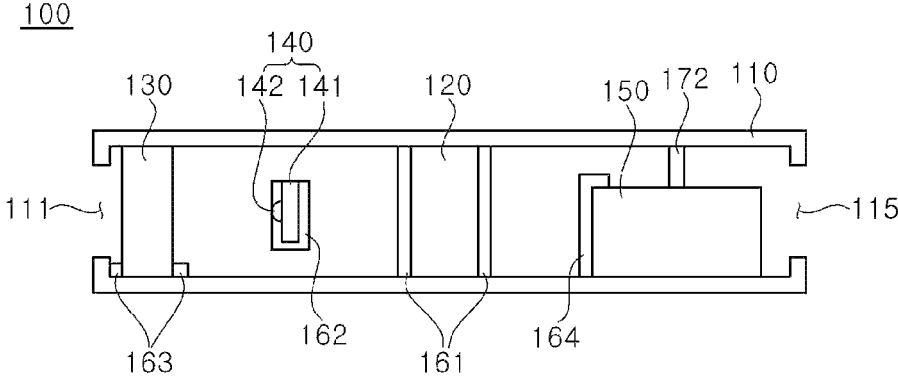
Figure 4:
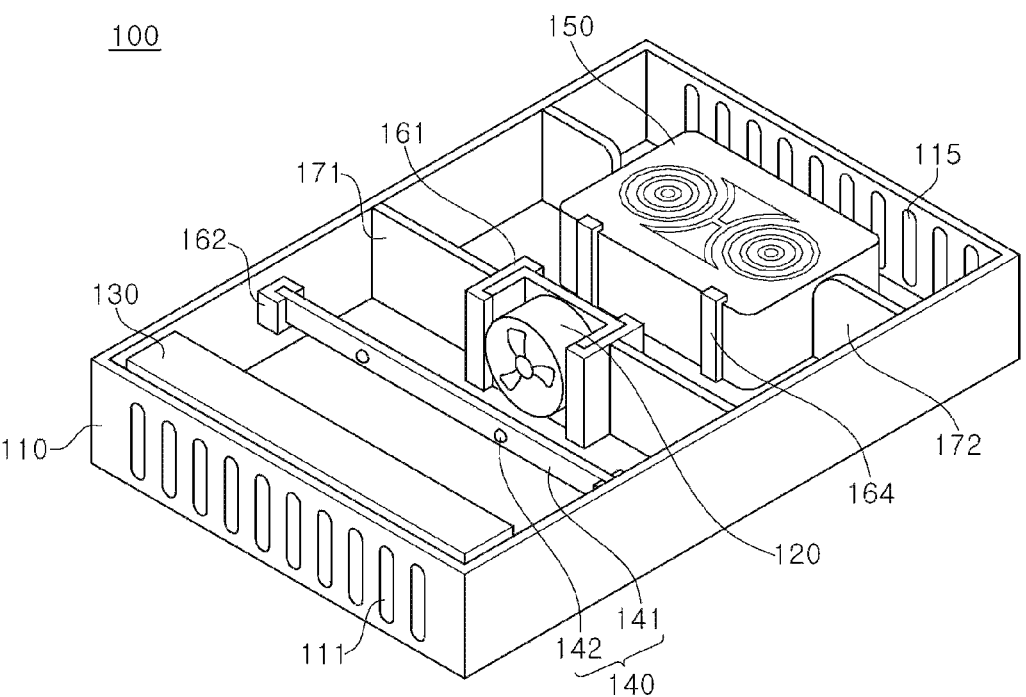

FIG. 1 is a perspective view of the deodorization module 100, FIG. 2 is a plan view of the deodorization module 100, FIG. 3 is a side view of the deodorization module 100, and FIG. 4 is a perspective view of the deodorization module 100.

Referring to FIG. 1 to FIG. 4, the deodorization module 100 includes a housing 110, a fan 120, a photocatalyst filter 130, a light source module 140, and an ion generator 150.

The housing 110 provides a space, in which deodorization of air is performed.

The housing 110 includes a suction port 111 formed on one side thereof and a discharge port 115 formed on the other side thereof. The suction port 111 and the discharge port 115 define an air flow channel. More specifically, the suction port 111 is a flow channel through which external air flows into the deodorization module 100. The discharge port 115 is a flow channel through which deodorized air is discharged from the deodorization module 100. Although the suction port 111 and the discharge port 115 are illustrated as being formed on the opposite sides of the housing 110 facing each other in FIG. 1, however, the inventive concepts are not limited to particular locations of the suction port 111 and the discharge port 115. In some exemplary embodiments, the locations of the suction port 111 and the discharge port 115 may be changed according to user selection.

Referring to FIG. 2 to FIG. 4, the fan 120, the photocatalyst filter 130, the light source module 140, and the ion generator 150 are disposed inside the housing 110.

The fan 120 is disposed between the light source module 140 and the ion generator 150. The fan 120 suctions air deodorized by the photocatalyst filter 130 and the light source module 140, and discharges the deodorized air towards the ion generator 150. The fan 120 guides an air flow inside the housing 110, such that air subjected to primary deodorization by the photocatalyst filter 130 and the light source module 140 is subjected to secondary deodorization by the ion generator 150. In addition, the fan 120 guides the interior air flow to prevent ions generated from the ion generator 150 from diffusing into the photocatalyst filter 130.

In the illustrated exemplary embodiment, the fan 120 is an axial flow fan. The axial flow fan is an air blower that generates an air flow in a direction parallel to a rotational axis of the fan, and can suction and discharge a large amount of air at a time. Although the fan 120 is illustrated as the axial flow fan, however, the inventive concepts are not limited thereto. In some exemplary embodiments, the fan 120 may be selected from any well-known fans in the art.

The photocatalyst filter 130 is disposed between the suction port 111 of the housing 110 and the fan 120.

The photocatalyst filter 130 has a bar structure formed with a plurality of through-holes. For example, the photocatalyst filter 130 is formed of a porous ceramic material. Alternatively, the photocatalyst filter 130 may be formed of a metal foam material including nickel (Ni), iron (Fe), aluminum (Al), chromium (Cr), and the like. A photocatalyst material is coated on a surface of the photocatalyst filter 130. The photocatalyst material includes at least one selected from the group of $TiO_2$, ZnO, $ZrO_2$, and $WO_3$. Alternatively, the photocatalyst filter 130 may be formed with the photocatalyst material.

The photocatalyst filter 130 is disposed between the suction port 111 and the light source module 140 to be placed close to the suction port 111. In addition, the photocatalyst filter 130 may be formed to have each side surface adjoining or adjacent to an inner surface of the housing 110. Accordingly, when air flow into the housing 110 through the suction port 111, air inevitably passes through the through-holes of the photocatalyst filter 130. As such, air having passed through the suction port 111 is completely deodorized by the photocatalyst filter 130, thereby improving deodorization efficiency of the deodorization module 100.

The light source module 140 is disposed between the fan 120 and the photocatalyst filter 130. The light source module 140 includes a substrate 141 and a UV light source 142.

The substrate 141 is electrically connected to the UV light source 142 and supplies power to the UV light source 142. For example, the substrate 141 may be a printed circuit board or a metal printed circuit board. In some exemplary embodiments, the light source module 140 may further include a heat sink for heat dissipation.

The UV light source 142 is mounted on one surface of the substrate 141, and emits UV light towards the photocatalyst filter 130. For example, the UV light source 142 is a light emitting diode chip. The UV light source 142 may be mounted singularly or in plural on the substrate 141. With a plurality of UV light sources 142 mounted on the substrate 141, the photocatalyst filter 130 may be uniformly irradiated with UV light. The number of UV light sources 142 may be varied as needed. Further, in the deodorization module including the plurality of UV light sources 142, at least one UV light source 142 may emit light having a different wavelength than other UV light sources 142. Further, in the deodorization module including the plural UV light sources 142, at least one UV light source 142 emits UV light having a sterilization effect in order to sterilize air.

According to the illustrated exemplary embodiment, UV light emitted from the UV light source 142 reacts with a photocatalyst substance of the photocatalyst filter 130 to generate active oxygen, such as superoxide ions and hydroxyl radicals. The active oxygen removes organic compounds generated as contaminants or odorous substances through decomposition thereof.

While passing through the through-holes of the photocatalyst filter 130 or a space between the photocatalyst filter 130 and the light source module 140, air is subjected to primary deodorization by the active oxygen generated by photocatalytic reaction. In addition, the air may further be subjected to sterilization.

The air subjected to primary deodorization by the photocatalyst filter 130 and the light source module 140 is forced to flow towards the ion generator 150 by the fan 120.

When the photocatalyst filter 130 is disposed too close to the light source module 140, UV light can reach only some portions of the photocatalyst filter 130. On the other hand, when the photocatalyst filter 130 is disposed too far from the light source module 140, the amount of UV light reaching the photocatalyst filter 130 can be reduced, thereby causing deterioration in deodorization efficiency.

When the light source module 140 is disposed too close to the fan 120, the light source module 140 can cause an increase in pressure loss of air suctioned into the fan 120.

Thus, the photocatalyst filter 130, the light source module 140, and the fan 120 are arranged in consideration of the area of the photocatalyst filter 130 irradiated with UV light, the amount of UV light irradiated thereon, and pressure loss of air caused by the light source module 140. A distance between the light source module 140 and the photocatalyst filter 130 is greater than a distance between the light source module 140 and the fan 120. For example, the distance between the light source module 140 and the photocatalyst filter 130 is 0.5 times or more the distance between the light source module 140 and the fan 120.

The ion generator 150 performs secondary deodorization of air that has been subjected to primary deodorization. The ion generator 150 emits a large amount of ions. The ions emitted from the ion generator 150 chemically react with organic compounds in the air. The air is deodorized and sterilized by chemical reaction between the ions and the organic compounds.

The ion generator 150 is disposed, such that an ion discharge port of the ion generator 150 faces the ceiling surface of the housing 110. Accordingly, while flowing to the discharge port 115 of the housing 110, air passes above the ion discharge port, and thus, can efficiently react with the ions.

In this manner, the deodorization module 100 performs double deodorization of air, thereby improving deodorization efficiency as compared with a deodorization module adapted to employ one of photocatalytic reaction and chemical reaction between ions and organic compounds. In addition, the deodorization module 100 can achieve sufficient deodorization of air through double deodorization of the air even when a large amount of air is intook into the housing 110.

The housing 110 may further include a first securing portion 161, a second securing portion 162, a third securing portion 163, a fourth securing portion 164, a first inner wall 171, and a second inner wall 172.

The first securing portion 161 is a fan securing portion adapted to secure the fan 120. The first securing portion 161 is formed to receive opposite sides of the fan 120 inserted thereinto. That is, the fan 120 is inserted into the first securing portion 161 and is secured in an upright posture inside the housing 110. The fan 120 inserted into the first securing portion 161 may have an upper surface adjoining a ceiling surface of the housing 110 and a lower surface adjoining a bottom surface of the housing 110.

Alternatively, the first securing portion 161 may be formed to receive the opposite sides and a lower surface of the fan 120 inserted thereinto. In this structure, the fan 120 is formed to have an upper surface adjoining the ceiling surface of the housing 110 and a lower surface adjoining a lower surface of the first securing portion 161. The lower surface of the first securing portion 161 adjoins the bottom surface of the housing 110.

The first securing portion 161 is formed at opposite sides of the first inner walls 171. The first inner wall 171 extends from one side of the first securing portion 161 to one side of the housing 110. Further, the first inner wall 171 extends from the other side of the first securing portion 161 to the other side of the housing 110. Further, the first inner wall 171 is formed to have an upper surface adjoining the ceiling surface of the housing 110 and a lower surface adjoining the bottom surface of the housing 110.

With such structures of the fan 120, the first securing portion 161 and the first inner wall 171, air subjected to primary deodorization by the photocatalyst filter 130 and the light source module 140 may be forced to flow towards the ion generator 150 only through the fan 120.

Photocatalytic reaction of the photocatalyst filter 130 and the light source module 140 can affections. More specifically, the ions can be decomposed by photocatalytic reaction. In addition, the ions can compete with organic compounds for photocatalytic reaction, thereby obstructing photocatalytic reaction of the organic compounds. As such, according to the illustrated exemplary embodiment, the fan 120, the first securing portion 161, and the first inner wall 171 may prevent the ions generated by the ion generator 150 from entering a space, in which the photocatalyst filter 130 and the light source module 140 are disposed. Accordingly, the deodorization module 100 according to the illustrated exemplary embodiment allows only the photocatalytic reaction of the organic compounds in air, thereby preventing deodorization efficiency through photocatalytic reaction from being deteriorated by ions.

The second securing portion 162 is a light source module securing portion adapted to secure the light source module 140. The second securing portion 162 is formed to receive opposite sides of the light source module 140 inserted thereinto. In addition, the second securing portion 162 secures the light source module 140 at a location where the largest area of the photocatalyst filter 130 can be irradiated with light emitted from the light source module 140. For example, the light source module 140 may be disposed at a position that corresponds to the center of the photocatalyst filter 130 when inserted into the second securing portion 162.

The second securing portion 162 may be formed as small as possible so long as the second securing portion 162 can secure the light source module 140. In this manner, the second securing portion 162 can reduce generation of eddy currents and disturbance against air flow.

The third securing portion 163 is a photocatalyst filter securing portion adapted to secure the photocatalyst filter 130. The third securing portion 163 is formed to receive opposite sides of the photocatalyst filter 130 inserted thereinto.

Alternatively, the third securing portion 163 is separated from one side of the housing 110 having the suction port 111 formed thereon, such that the photocatalyst filter 130 can be inserted into a space between the third securing portion 163 and the housing 110.

Alternatively, when all side surfaces of the photocatalyst filter 130 contact inner surfaces of the housing 110, the third securing portion 163 may be omitted.

The fourth securing portion 164 is an ion generator securing portion adapted to secure the ion generator 150. The fourth securing portion 164 is formed to surround a portion of a side surface of the ion generator 150. However, the inventive concepts are not limited to a particular structure of the fourth securing portion 164, as long as the ion generator 150 can be secured within the housing 110.

The second inner wall 172 extends from the opposite sides of the housing 110 to adjoin opposite sides of the ion generator 150. In addition, the second inner wall 172 is formed to have a greater height than the ion generator 150. This structure of the second inner wall 172 allows all of air having passed through the fan 120 to pass through a space between the second inner walls 172. Here, since the ion discharge port is placed on an upper surface of the ion generator 150, all air passes above the ion discharge port. Thus, all of the air passing through the space between the second inner walls 172 reacts with ions, thereby improving deodorization efficiency of the deodorization module 100.

In the illustrated exemplary embodiment, the first to fourth securing portions 161 to 164, the first inner wall 171, and the second inner wall 172 are illustrated as separate components. However, the inventive concepts are not limited thereto, and in some exemplary embodiments, at least one or more of the first to fourth securing portions 161 to 164, the first inner wall 171 and the second inner wall 172 may be integrally formed with the housing 110.

In some exemplary embodiments, the deodorization module 100 may have a control substrate and electric wires disposed therein. The control substrate is connected to each of the components by the electric wire. The control substrate supplies electric power to the components through the electric wires or stops power supply thereto.

As described above, the deodorization module 100 according to the illustrated exemplary embodiment performs double deodorization of air using the photocatalyst and the ions, thereby improving deodorization efficiency. Further, the deodorization module 100 may have optimized deodorization efficiency through optimal arrangement of the photocatalyst filter 130, the light source module 140, and the fan 120. Further, the deodorization module 100 performs double deodorization of air through the first inner wall 171 and the second inner wall 172 when the air passes through the interior of the housing 110, thereby improving deodorization efficiency.

Hereinafter, repeated descriptions of substantially the same components already described above will be omitted to avoid redundancy.

Figure 5:
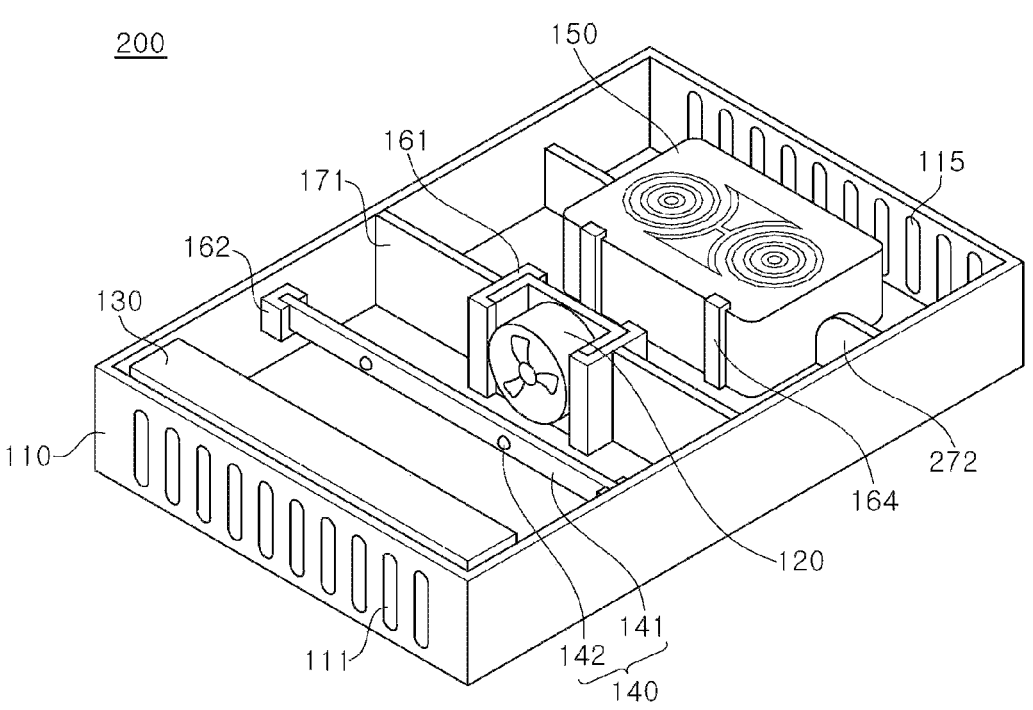
FIG. 5 is an exemplary view of a deodorization module according to a second exemplary embodiment.

FIG. 5 is an exemplary view of a deodorization module according to a second exemplary embodiment.

Referring to FIG. 5, a second inner wall 272 is formed have the same height as the ion generator 150 or a smaller height than the ion generator 150. That is, the second inner wall 272 is placed at the same height as or at a lower height than the ion discharge port of the ion generator 150.

Ions emitted from the ion generator 150 efficiently diffuse due to an ion concentration difference in air. However, the ion generator 150 has a larger volume than other components, and the ion discharge port is placed at a higher location. Accordingly, despite efficient diffusion of ions, it is difficult to achieve uniform diffusion of the ions to the bottom surface of the housing 110. Thus, the second inner wall 272 according to the illustrated exemplary embodiment prevents the ions from diffusing to the bottom surface of the housing 110, thereby securing a uniform concentration of the ions at a predetermined height or more inside the housing 110.

However, if the second inner wall 272 has an excessive height, an air flow channel is narrowed, thereby causing loss of air pressure.

Thus, in order to secure efficient diffusion of the ions without loss of air pressure, the second inner wall 272 is formed to have the same height as or a smaller height than the ion generator 150.

With this structure of the second inner wall 272, air can react with the ions through as large an area as possible without loss of air pressure, thereby improving deodorization efficiency of the deodorization module 200.

Figure 6:
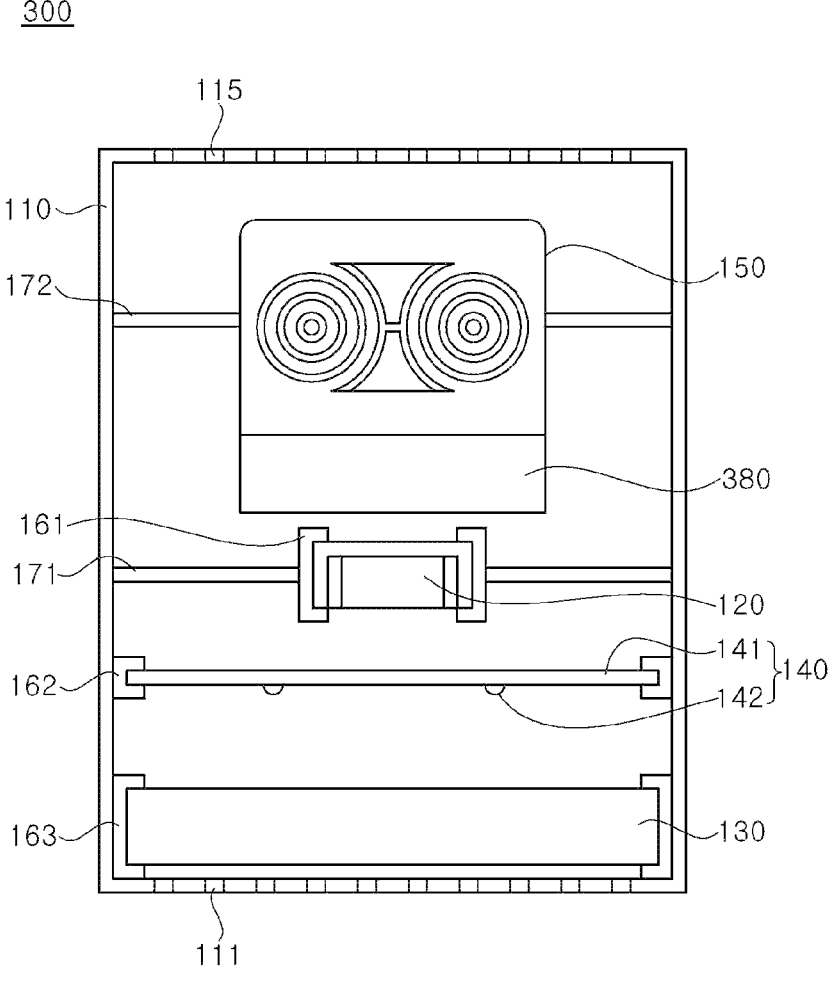
FIG. 6 and FIG. 7 are exemplary views of a deodorization module according to a third exemplary embodiment.
Figure 7:
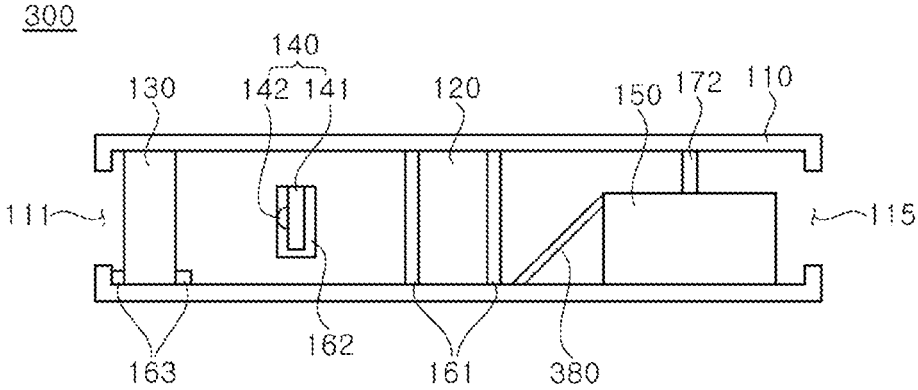
Figure 8:
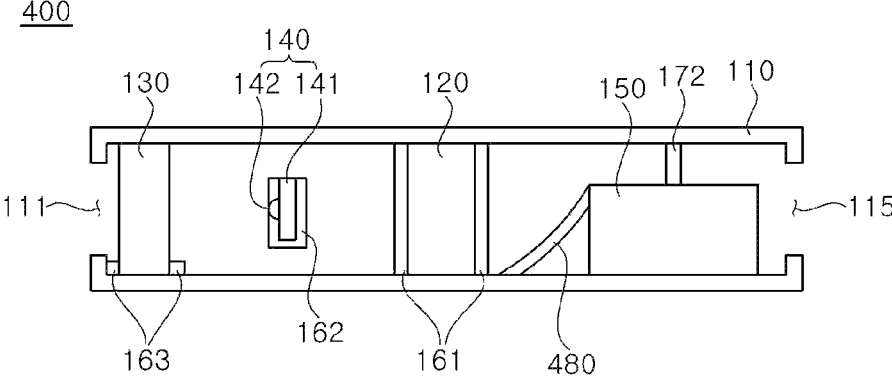
FIG. 8 is an exemplary view of a deodorization module according to a fourth exemplary embodiment.

FIG. 6 to FIG. 8 are exemplary views of deodorization modules according to third and fourth exemplary embodiments.

FIG. 6 and FIG. 7 are a plan view and a side view of a deodorization module 300 according to the third exemplary embodiment, and FIG. 8 is a side view of a deodorization module 400 according to the fourth exemplary embodiment.

The deodorization modules 300 and 400 according to the third and fourth exemplary embodiments include flow channel guides 380 and 480, respectively.

The flow channel guide 380 or 480 is formed between the fan 120 and the ion generator 150. The flow channel guide 380 or 480 has one side adjoining the bottom surface of the housing 110 and the other side adjoining an upper end of one side of the ion generator 150. As such, the flow channel guides 380 and 480 have a slanted structure, in which one side of the flow channel guide has a different height than the other side thereof.

The deodorization module 300 according to the third exemplary embodiment has a flow channel guide 380 that has a slanted upper surface.

The deodorization module 400 according to the fourth exemplary embodiment has a flow channel guide 480 that has a downwardly concave upper surface.

Air discharged from the fan 120 is guided towards the upper surface of the ion generator 150 by the flow channel guide 380 or 480. With this structure, the flow channel guide 380 or 480 prevents generation of eddy currents and loss of air pressure due to collision of air to the side surface of the ion generator 150. Further, by minimizing an air flow disturbance factor using the flow channel guide 380 or 480, all air having passed through the fan 120 can be deodorized by the ion generator 150. Thus, the deodorization module 300 or 400 can have improved deodorization efficiency through the flow channel guide 380 or 480. In particular, the deodorization module 400 according to the fourth exemplary embodiment can more effectively prevent loss of air pressure through the concave structure of the flow channel guide 480.

Figure 9:
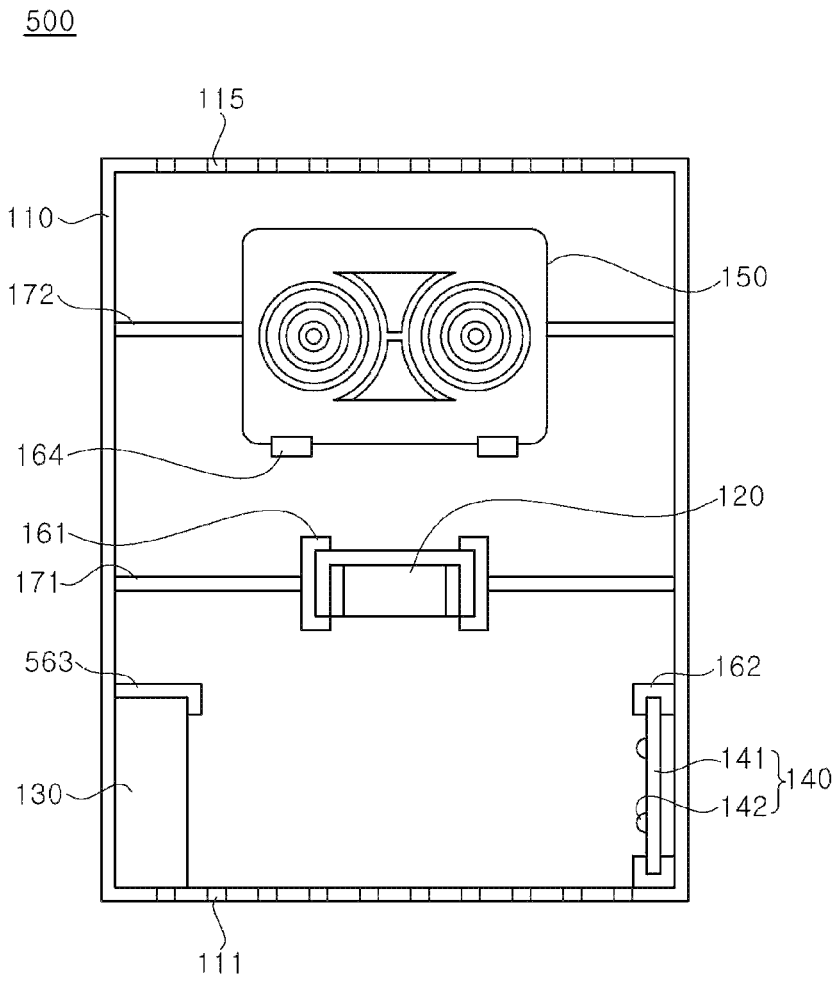
FIG. 9 is an exemplary view of a deodorization module according to a fifth exemplary embodiment.
Figure 10:
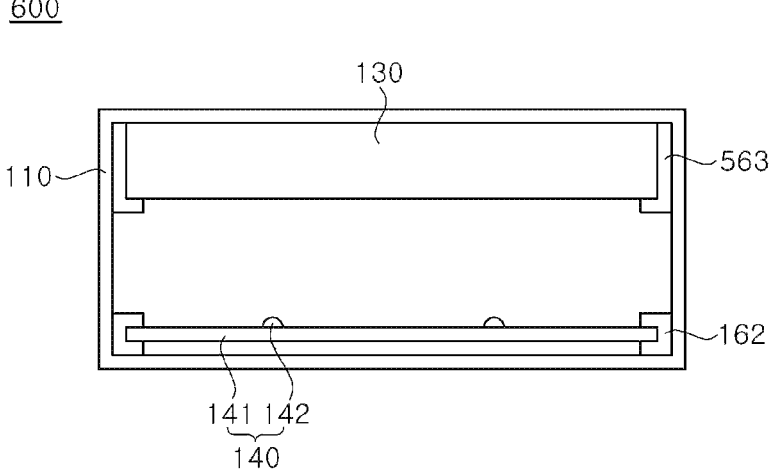
FIG. 10 is an exemplary view of a deodorization module according to a sixth exemplary embodiment.
Figure 11:
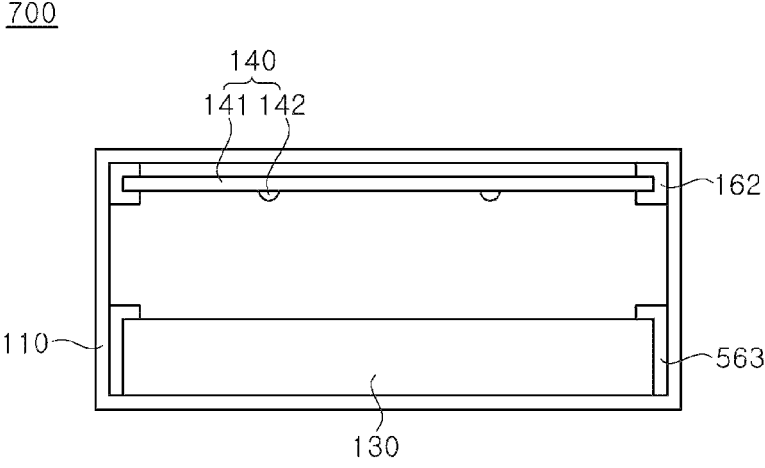
FIG. 11 is an exemplary view of a deodorization module according to a seventh exemplary embodiment.

FIG. 9 to FIG. 11 are exemplary views of deodorization modules according to fifth to seventh exemplary embodiments.

In the deodorization module 500 according to the fifth exemplary embodiment shown in FIG. 9, the photocatalyst filter 130 is disposed on one side of the housing 110 and the light source module 140 is disposed on the other side of the housing 110 inside the housing 110.

In the deodorization module 600 according to the sixth exemplary embodiment shown in FIG. 10, the photocatalyst filter 130 is disposed on the bottom surface of the housing 110 and the light source module 140 is disposed on the ceiling surface of the housing 110.

In the deodorization module 700 according to the seventh exemplary embodiment shown in FIG. 11, the photocatalyst filter 130 is disposed on the ceiling surface of the housing 110 and the light source module 140 is disposed on the bottom surface of the housing 110.

In FIG. 10 and FIG. 11, only the locations of the photocatalyst filter 130 and the light source module 140 are shown. Arrangement of the other components is the same as those described above with reference to FIGS. 1 to 9.

In the fifth to seventh exemplary embodiments, the locations of the second securing portion 162 and the third securing portion 563 are changed depending upon the locations of the light source module 140 and the photocatalyst filter 130.

Further, when the photocatalyst filter 130 is disposed to contact an inner surface of the housing 110, the third securing portion 563 may have a different structure from the third securing portion 163 already described above. More particularly, referring to FIG. 9 to FIG. 11, the third securing portion 563 protrudes from the inner surface of the housing 110 and is bent at one end thereof. In FIG. 9, since one side and a rear surface of the photocatalyst filter 130 contact the inner surface of the housing 110, the third securing portion 563 is formed to allow only the other side of the photocatalyst filter 130 to be inserted thereinto. In FIG. 10 and FIG. 11, since only the rear surface of the photocatalyst filter 130 contacts the inner surface of the housing 110, the third securing portion 563 is formed to allow opposite sides of the photocatalyst filter 130 to be inserted thereinto.

As such, the structure of the third securing portion 563 may also be changed depending upon the location of the photocatalyst filter 130. In this case, not only the structure of the photocatalyst filter 130, but also the structures of the other securing portions may be changed, depending upon the structures and locations of the components.

For heat dissipation, the light source module 140 may be separated from the inner surface of the housing 110. Alternatively, with a sufficient heat dissipation function, the light source module 140 may not be separated from the inner surface of the housing 110.

The photocatalyst filter 130 may be disposed to face the light source module 140 and may be irradiated with UV light emitted from the light source module 140. Further, the suction port 111 of the housing 110 is placed between the photocatalyst filter 130 and the light source module 140. Accordingly, air having entered the housing 110 through the suction port 111 is suctioned into the fan 120 through a space between the photocatalyst filter 130 and the light source module 140.

Here, while air flows through the space between the photocatalyst filter 130 and the light source module 140, the air is deodorized and sterilized through reaction with active oxygen generated through photocatalytic reaction. In addition, when the light source module 140 emits UV light having a sterilization function, the air is sterilized by the UV light while flowing through the space between the photocatalyst filter 130 and the light source module 140.

In the deodorization modules 500, 600, 700 according to exemplary embodiments, no component capable of disturbing an air flow is disposed between the suction port 111 and the fan 120. Accordingly, the deodorization modules 500, 600, 700 according to the exemplary embodiments have high air inflow rates and may suppress loss of air pressure, thereby improving deodorization efficiency. In addition, the high air inflow rates of the deodorization modules 500, 600, 700 allow rapid circulation of surrounding air, thereby providing efficiency in air deodorization in a space, such as a refrigerator, a wardrobe, a vehicle, and the like.

Further, the deodorization modules 500, 600, 700 are efficient for environments including molecules having high reaction rates, such as in the interior of a vehicle.

Figure 12:
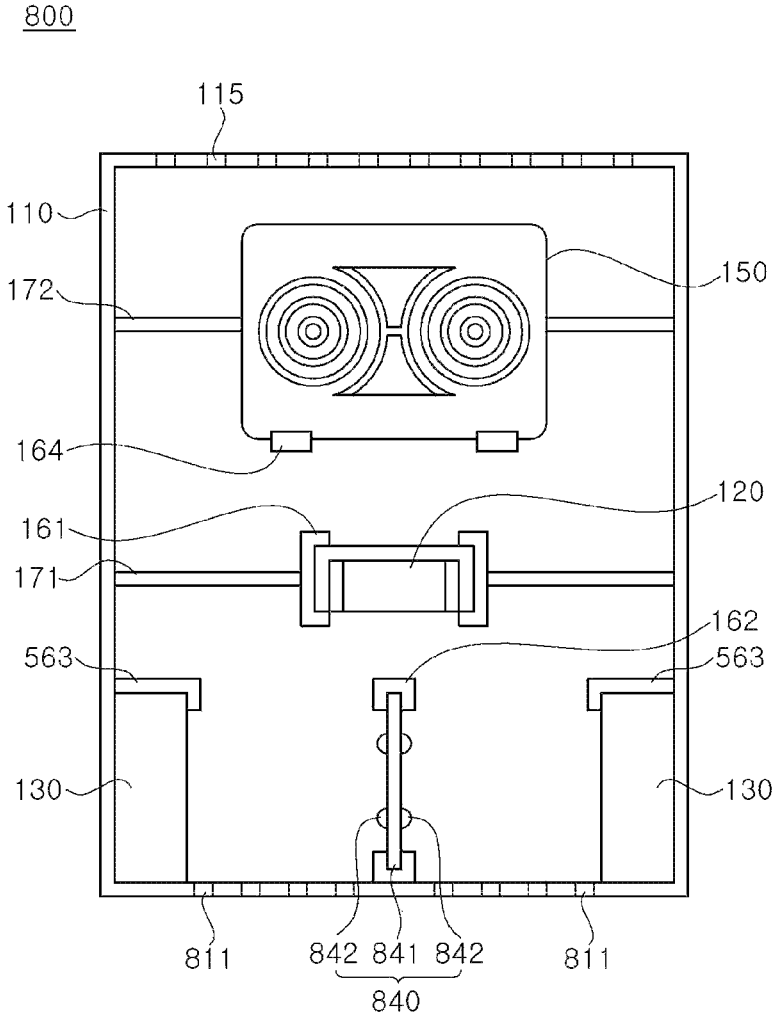
FIG. 12 is an exemplary view of a deodorization module according to an eighth exemplary embodiment.
Figure 13:
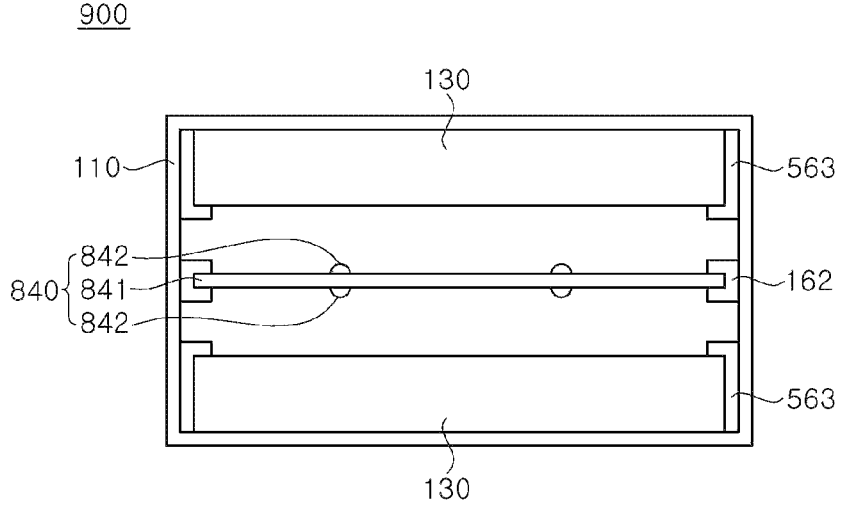
FIG. 13 is an exemplary view of a deodorization module according to a ninth exemplary embodiment.

FIG. 12 and FIG. 13 are exemplary views of deodorization modules according to eighth and ninth exemplary embodiments.

In the deodorization module 800 according to the eighth exemplary embodiment shown in FIG. 12, the photocatalyst filters 130 are disposed on one side and the other side of the housing 110 inside the housing 110, respectively, and a light source module 840 is disposed between the two photocatalyst filters 130.

In the deodorization module 900 according to the ninth exemplary embodiment shown in FIG. 13, the photocatalyst filters 130 are disposed on the ceiling and bottom surfaces of the housing 110, respectively, and a light source module 840 is disposed between the two photocatalyst filters 130.

In the eighth and ninth exemplary embodiments, the light source module 840 includes UV light sources 842 mounted on both surfaces of a substrate 841. FIG. 12 and FIG. 13 each shows a structure, in which the UV light source 842 mounted on one surface of the substrate 841 is placed at the same location as the UV light source 842 mounted on the other surface of the substrate 841. Alternatively, for dissipation of heat from the light source module 840, the UV light source 842 on the one surface of the substrate 841 and the UV light source 842 on the other surface of the substrate 841 may be alternately arranged.

According to the eighth exemplary embodiment, the UV light source 842 on the one surface of the substrate 841 emits UV light towards the photocatalyst filter 130 on the one side of the housing 110 inside the housing 110. Further, the UV light source 842 on the other surface of the substrate 841 emits UV light towards the photocatalyst filter 130 on the other side of the housing 110 inside the housing 110.

According to the ninth exemplary embodiment, the UV light source 842 mounted on one surface of the substrate 841, that is, on an upper surface of the substrate 841, emits UV light towards the photocatalyst filter 130 on the ceiling surface of the housing 110. In addition, the UV light source 842 mounted on the other surface of the substrate 841, that is, on a lower surface of the substrate 841, emits UV light towards the photocatalyst filter 130 on the bottom surface of the housing 110.

In the eighth and ninth exemplary embodiments, the numbers and locations of the second securing portions 162 and the third securing portions 563 may be changed depending upon the numbers and locations of the light source modules 840 and the photocatalyst filters 130.

In this structure of the deodorization module 800 and 900, the distance between the photocatalyst filter 130 and the light source module 840 is shorter than the distance therebetween in the fifth exemplary embodiment. As such, the photocatalyst filter 130 may be irradiated with a sufficient intensity of UV light.

Further, by the two photocatalyst filters 130 and the light source module 840 disposed therebetween, air having passed through suction ports 811 is divided into two air streams at both sides of the light source module 840 and flow towards the fan 120. Here, two air channels are not completely blocked by the light source module 840 and the second securing portion 162. Alternatively, the two air channels may be completely blocked by changing the structures of the light source module 840 and the second securing portion 162 or by adding other components.

Further, in the deodorization module 800 and 900, the suction ports 811 are formed on one side surface of the housing 110 to be placed at opposite sides thereof with respect to the light source module 840. That is, each of the suction ports 811 may be formed between the light source module 840 and the photocatalyst filter 130. Accordingly, it is possible to prevent the suction ports 811 from being placed at unsuitable locations.

Each of the deodorization module 800, 900 according to the exemplary embodiments includes the two photocatalyst filters 130 and the light source module 840 disposed therebetween, thereby improving deodorization efficiency through irradiation of the photocatalyst filters 130 with sufficient intensity of UV light. Further, the deodorization modules 800, 900 allow air to be divided into two air streams by the light source module 840 and to flow along two air channels, in which photocatalytic reaction occurs, thereby improving deodorization efficiency.

Further, since the deodorization modules 800, 900 do not have any component that may disturb the flow of air between the suction ports 811 and the fan 120, the deodorization modules 800, 900 have a high air inflow rate, thereby allowing rapid circulation of surrounding air. Further, the deodorization modules 800, 900 employ the two photocatalyst filters 130. Thus, the deodorization module, 800, 900 allow rapid deodorization of air by rapid circulation of air and the two photocatalyst filters 130, thereby improving deodorization efficiency.

In eight and ninth exemplary embodiments, the light source module 840 is illustrated as including one substrate 841 having the UV light sources 842 mounted on both surfaces thereof. Alternatively, the light source module 840 may include two substrates 841 each having the UV light source 842 on one surface thereof and disposed, such that the other surface of one substrate 841 adjoins the other surface of the other substrate 841.

Figure 14:
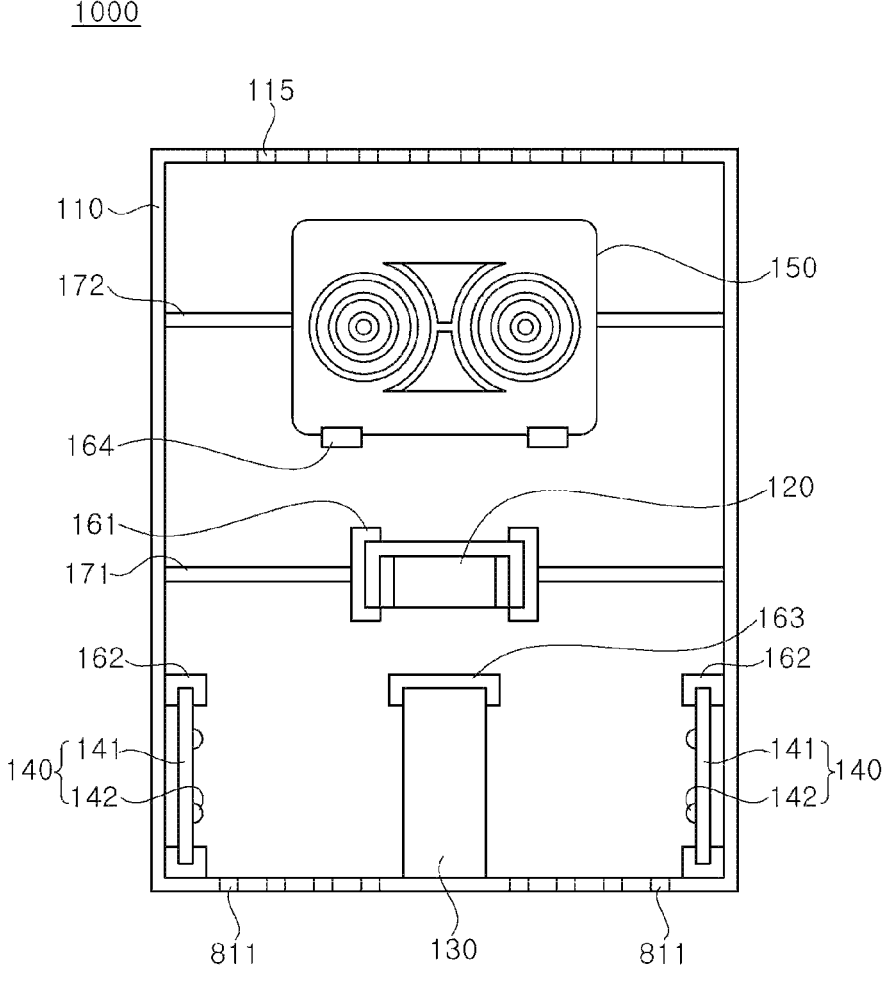
FIG. 14 is an exemplary view of a deodorization module according to a tenth exemplary embodiment.
Figure 15:
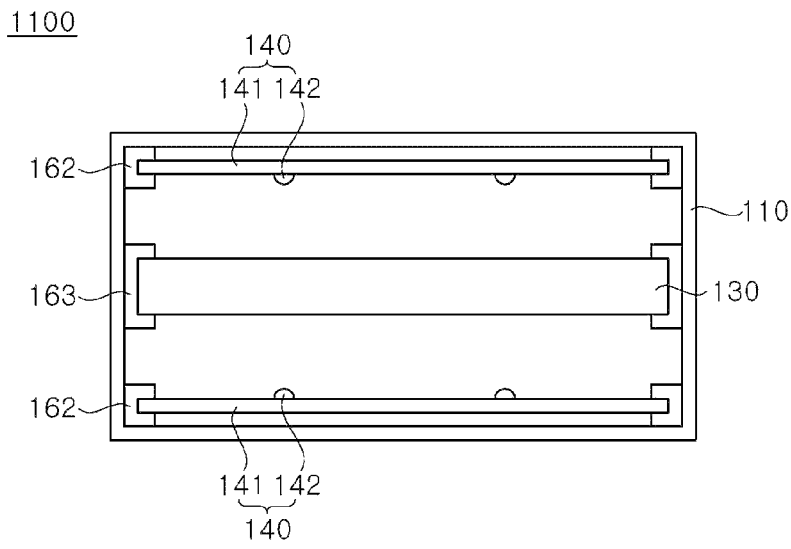
FIG. 15 is an exemplary view of a deodorization module according to an eleventh exemplary embodiment.

FIG. 14 and FIG. 15 are exemplary views of deodorization modules according to tenth and eleventh exemplary embodiments.

Referring to FIG. 14, the deodorization module 1000 according to the tenth exemplary embodiment includes the light source modules 140 respectively mounted on one side and the other side of the housing 110 inside the housing 110. Further, the deodorization module 100 includes the photocatalyst filter 130 disposed between the two light source modules 140.

Referring to FIG. 15, the deodorization module 1100 according to the eleventh exemplary embodiment includes the light source modules 140 disposed on the ceiling and bottom surfaces of the housing 110, respectively. Further, the deodorization module 1100 includes the photocatalyst filter 130 disposed between the two light source modules 140.

Like the deodorization modules 800, 900 according to the eighth and ninth exemplary embodiments, each of the deodorization modules 1000, 1100 according to the tenth and eleventh exemplary embodiments has a shorter distance between the photocatalyst filter 130 and each of the light source modules 140 than that of the deodorization module according to the fifth exemplary embodiment. Accordingly, the photocatalyst filter 130 can be irradiated with sufficient intensity of UV light emitted from the light source modules 140. Further, air is subjected to deodorization while flowing along the channels between the photocatalyst filter 130 and the light source modules 140.

Furthermore, in the deodorization module 1000 and 1100, a suction port 811 may be formed between the photocatalyst filter 130 and each of the light source modules 140. Since the photocatalyst filter 130 has a greater thickness, the suction port 811 can be partially blocked by the photocatalyst filter 130. Since the air cannot pass through the portion of the suction port 811 blocked by the photocatalyst filter 130, the suction port 811 is not formed at a location at which the photocatalyst filter 130 is disposed. Accordingly, the deodorization modules 1000, 1100 may obviate unnecessary machining of the housing 110. Further, since the housing 110 has a non-processed portion between the suction ports 811 on the one side of the housing 110, on which the suction ports 811 are formed, the one side of the housing 110 according to the illustrated exemplary embodiment has a stronger structure than the one side of the housing 110 according to the other exemplary embodiments, on which the suction ports 811 are formed in a large area. Accordingly, the deodorization module 1000 and 1100 according to the exemplary embodiments can prevent the one side of the housing 110 having the suction ports 811 formed thereon from being damaged by external impact.

Figure 16:
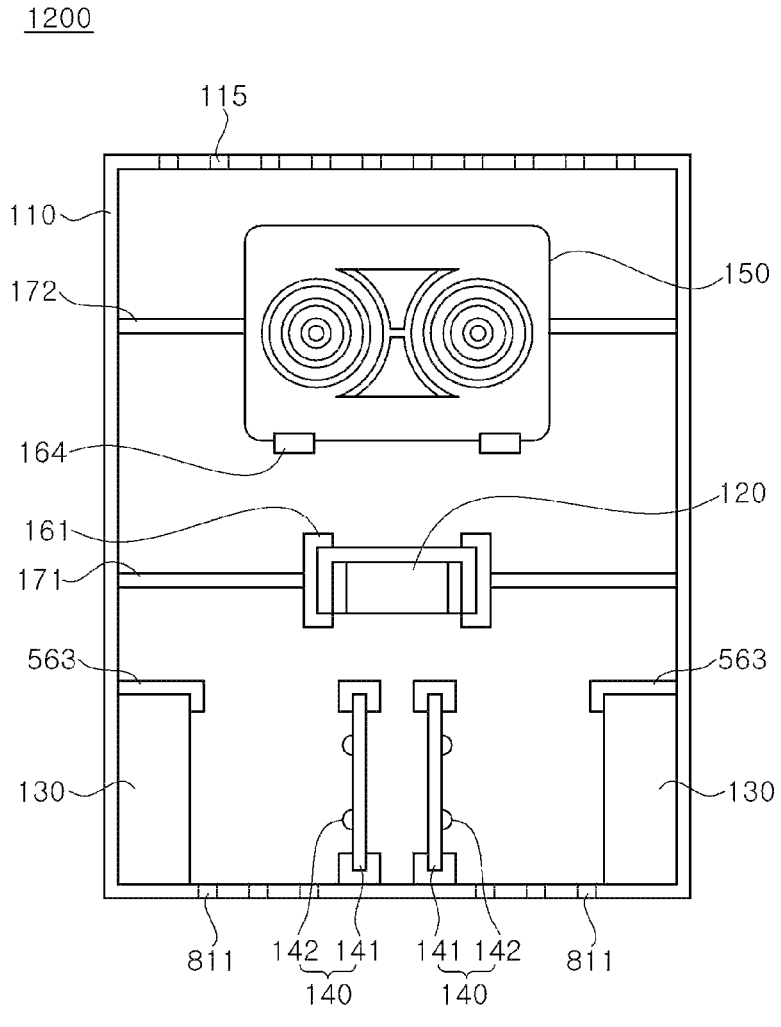
FIG. 16 is an exemplary view of a deodorization module according to a twelfth exemplary embodiment.

FIG. 16 is an exemplary view of a deodorization module according to a twelfth exemplary embodiment of the present invention.

In the deodorization module 1200 according to the twelfth exemplary embodiment, the photocatalyst filters 130 are disposed on one side and the other side of the housing 110 inside the housing 110, respectively. In addition, the deodorization module 1200 includes two light source modules 140 between the two photocatalyst filters 130.

The two light source modules 140 are separated from each other, and emit UV light in opposite directions, respectively. That is, each of the light source modules 140 is disposed to emit UV light towards the photocatalyst filter 130 adjacent thereto. Accordingly, the light source modules 140 are disposed closer to the photocatalyst filter 130, thereby allowing more active photocatalytic reaction.

Further, the deodorization module 1200 is configured to allow air to flow along a channel formed between the light source module 140 and the photocatalyst filter 130. To this end, a suction port 811 may be formed between each of the light source modules 140 and the photocatalyst filter 130.

Accordingly, in the deodorization module 1200, the photocatalyst filters 130 may be irradiated with sufficient intensity of UV light, and air flows along the two channels in which photocatalytic reaction occurs, thereby improving deodorization efficiency of the air.

Further, since there is no component that may disturb an air flow between the suction port 811 and the fan 120, the deodorization module 1200 has a high air inflow rate, thereby allowing rapid circulation of surrounding air. In addition, the deodorization module 1200 employs the two photocatalyst filters 130. Thus, the deodorization module 1200 allows rapid deodorization of air by rapid circulation of air and the two photocatalyst filters 130, thereby improving deodorization efficiency.

The distance between the two light source modules 140 may be changed in consideration of the intensity of UV light for photocatalytic reaction and the amount of air to be deodorized.

In the deodorization module 1200 according to the twelfth exemplary embodiment, the suction port 811 may be formed on one side of the housing 110 between each of the light source modules 140 and the photocatalyst filter 130 corresponding thereto. That is, in the deodorization module 1200, the suction port 811 is not formed at a location on the one side of the housing 110 corresponding to a region between the two light source modules 140. Accordingly, the deodorization module 1200 according to the twelfth exemplary embodiment can also prevent the housing 110 from being damaged by external impact.

Figure 17:
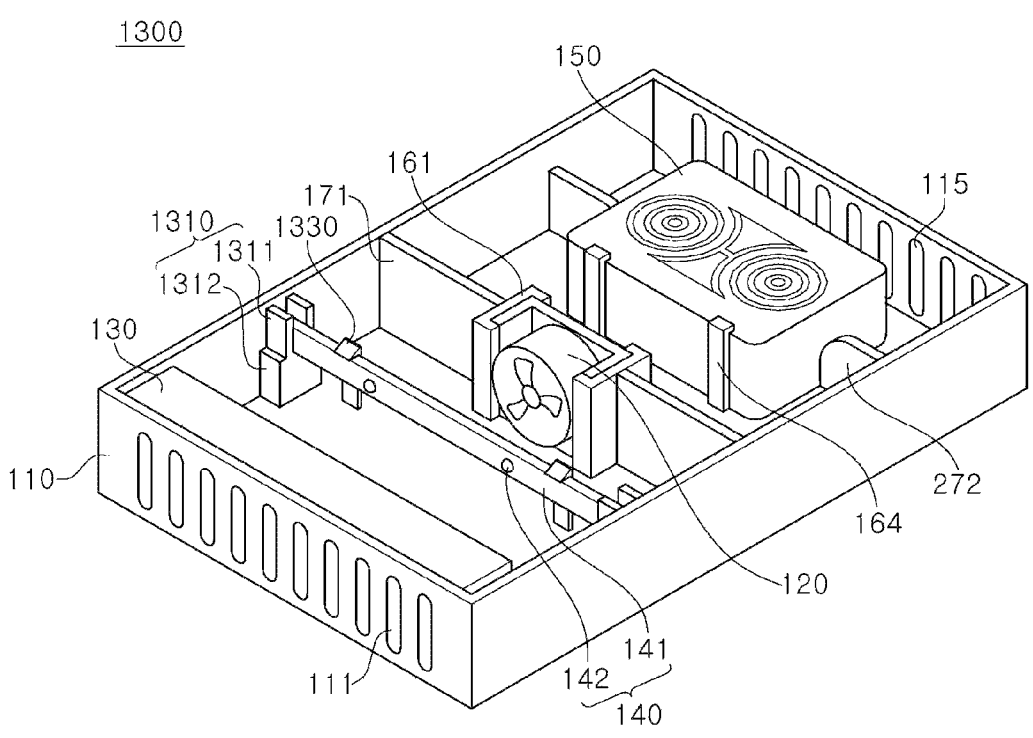
FIG. 17 and FIG. 18 are exemplary views of a deodorization module according to a thirteenth exemplary embodiment.
Figure 18:
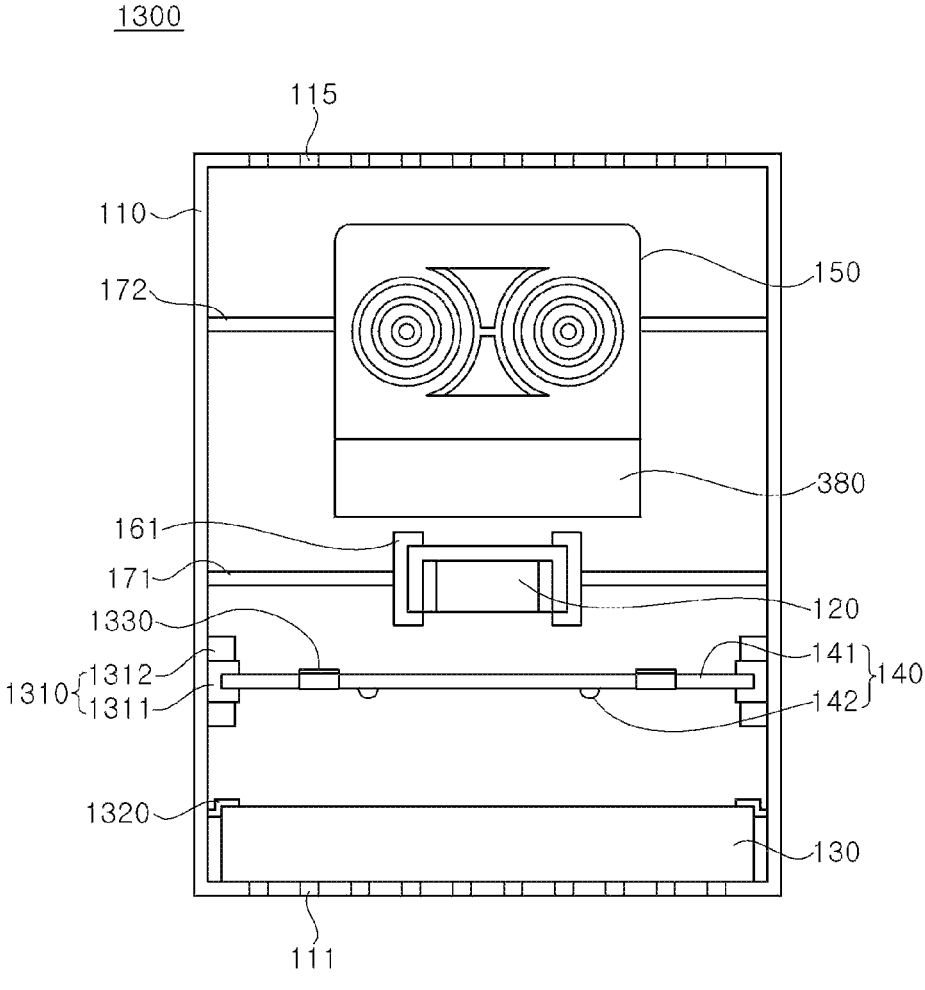

FIG. 17 and FIG. 18 are exemplary views of a deodorization module according to a thirteenth exemplary embodiment.

Referring to FIG. 17 and FIG. 18, in the deodorization module 1300 according to the thirteenth exemplary embodiment, the light source module 140 is secured by a second securing portion 1310 and a fifth securing portion 1330. Here, the second securing portion 1310 is a first light source module securing portion formed to receive opposite sides of the light source module 140 inserted thereinto. In addition, the fifth securing portion 1330 is a second light source module securing portion formed to contact an upper side surface of the light source module 140.

The second securing portion 1310 includes an insertion portion 1311 and a support portion 1312. In the second securing portion 1310, the insertion portion 1311 receives the opposite sides of the light source module 140 inserted thereinto. In the second securing portion 1310, the support portion 1312 is formed under the insertion portion 1311 to support the insertion portion 1311. The height of the light source module 140 may be changed depending upon the height of the support portion 1312. With this structure, the support portion 1312 prevents the light source module 140 from falling downwards from the housing 110.

The fifth securing portion 1330 protrudes upwards from the bottom surface of the housing 110. An upper end of the fifth securing portion 1330 has a bent shape. An inner surface of the bent upper end of the fifth securing portion 1330 contacts the upper side surface of the light source module 140. Alternatively, the fifth securing portion 1330 may be formed of a resilient material, such that the inner surface of the bent upper end of the fifth securing portion 1330 compresses the upper side surface of the light source module 140. The fifth securing portion 1330 prevents the light source module 140 from being separated upwards from the housing 110.

According to the illustrated exemplary embodiment, even when the deodorization module 1300 is reversed or exposed to impact, the light source module 140 is maintained in a secured state at a predetermined location by the second securing portion 1310 and the fifth securing portion 1330.

Further, in the deodorization module 1300 according to the thirteenth exemplary embodiment, the photocatalyst filter 130 is secured by third securing portions 1320. Here, each of the third securing portions 1320 is a photocatalyst filter securing portion adapted to secure the photocatalyst filter 130, and is separated from the suction port 111 of the housing 110. The photocatalyst filter 130 is inserted into a space between the third securing portions 1320 and an inner surface of the housing 110 having the suction port 111 thereon, and is secured inside the housing 110.

The third securing portions 1320 are formed at locations separated from the suction port 111 to protrude inwards from the opposite sides of the housing 110 inside the housing 110, respectively. Each of the third securing portions 1320 is bent to have a multi-step structure. One end of each of the third securing portions 1320 adjoins one side or the other side of the housing 110, and the other end of one third securing portion 1320 faces the other end of the other third securing portion 1320. In addition, an inner surface of a bent portion of the third securing portion 1320 partially surrounds side and rear surfaces of the photocatalyst filter 130. A distance between the bent portions of the third securing portions 1320 may be changed depending upon the width of the photocatalyst filter 130. Accordingly, even when the photocatalyst filter 130 has a smaller width than an inner width of the housing 110, the photocatalyst filter 130 can be secured inside the housing 110 by the third securing portions 1320.

Further, a front surface of the photocatalyst filter 130 is brought into close contact with the inner surface of the housing 110, on which the suction port 111 is formed. Accordingly, the deodorization module 1300 allows all air having passed through the suction port 111 to pass through the photocatalyst filter 130, thereby improving deodorization efficiency thereof.

As such, the deodorization module according to the exemplary embodiments of the present invention may be mounted on an electronic device. As used herein, the electronic device refers to an apparatus, such as a vehicle, a refrigerator, and the like, which has an interior space and is operated by electricity. For example, the electronic device includes an electronic device housing defining an interior space, and the deodorization module is received in the electronic device housing. The deodorization module suctions and deodorizes air in the interior space of the electronic device housing, followed by discharging the air into the electronic device housing. Through this operation, the deodorization module can deodorize air in an interior space of the electronic device.

Furthermore, the deodorization module may be provided not only to the electronic device, but also to furniture, a room space receiving articles, or an activity space of persons. For example, the deodorization module may be disposed inside a drawer or a room.

Although certain exemplary embodiments and implementations have been described herein, other embodiments and modifications will be apparent from this description. Accordingly, the inventive concepts are not limited to such embodiments, but rather to the broader scope of the appended claims and various obvious modifications and equivalent arrangements as would be apparent to a person of ordinary skill in the art.

The invention claimed is:

1. A deodorization apparatus comprising:
a housing having an inlet at a first side of the housing, an outlet at a second side of the housing that is different from the first side of the housing, the housing having a width along a direction and a first sidewall and a second sidewall that are spaced apart from each other along the direction;
a fan disposed between the inlet and the outlet;
a filter disposed between the inlet and the fan and configured to receive an air from the inlet and provide a filtered air, the filter comprising two sidewalls that adjoin to the first sidewall and the second sidewall of the housing;
an ion generator disposed between the filter and the outlet and configured to receive the filtered air, the ion generator having an ion discharge port facing a ceiling surface of the housing;
a first holder disposed in the housing and configured to include a first region and a second region that are disposed at two opposite sides of the fan, respectively;
a second holder disposed in the housing and configured to be connected with the ion generator; and
a first wall including a first region extending from the first region of the first holder to be in contact with the first side wall of the housing and a second region extending from the second region of the first holder to the second sidewall of the housing, the first wall configured to allow the filtered air to move toward the ion generator through a region defined by the first holder and the second holder.

2. The deodorization apparatus of claim 1, wherein the first wall adjoins a bottom region of the housing.

3. The deodorization apparatus of claim 1, wherein the first wall is disposed to be in contact with the first holder.

4. The deodorization apparatus of claim 1, wherein first wall is disposed on one side the fan.

5. The deodorization apparatus of claim 1, further comprising a second wall extended from a third side of the housing.

6. The deodorization apparatus of claim 5, wherein the ion generator is configured to generate ions such that the filtered air reacts with the ions while passing the second region.

7. The deodorization apparatus of claim 1, further comprising a light emitter disposed in the housing.

8. The deodorization apparatus of claim 7, wherein the light emitter includes a plurality of light emitting sources that is configured to emit light having different wavelengths from each other.

9. The deodorization apparatus of claim 7, wherein the light emitter is configured to emit the light toward the filter.

10. A deodorization apparatus comprising:
a housing having an inlet at a first side of the housing and an outlet at a second side of the housing that is different from the first side of the housing, the housing having a width along a direction and a first sidewall and a second sidewall that are spaced apart from each other along the direction;
a filter disposed between the inlet and the outlet and comprising two sidewalls that adjoin to the first sidewall and the second sidewall of the housing;
a fan and an ion generator that are disposed along a direction from the inlet to the outlet, the ion generator having an ion discharge port facing a ceiling surface of the housing;
a first holder including a first region and a second region that are in contact with a first region and a second region of the fan, respectively, the first region and the second region of the first holder disposed at two opposite sides of the fan;
a second holder disposed in the housing and configured to be in contact with the ion generator;
a first wall extending from the first region of the first holder to be in contact with a sidewall of the housing that connects the inlet and the outlet, the first wall configured to provide a region that is inside of the housing and guide an air to flow toward the ion generator through the region.

11. The deodorization apparatus of claim 10, wherein the first wall adjoins a bottom region of the housing.

12. The deodorization apparatus of claim 10, wherein the first wall is disposed on one side of the fan.

13. The deodorization apparatus of claim 10, further comprising a second wall extended from a third side of the housing such that a second region is disposed between the second wall and the outlet.

14. The deodorization apparatus of claim 13, wherein the ion generator is configured to generate ions such that a filtered air reacts with the ions while passing the second region.

15. A deodorization apparatus, comprising:
a housing having a width along a direction and having an inlet at a first side of the housing, an outlet at a second side of the housing that is different from the first side of the housing, and a first sidewall and a second sidewall that are spaced apart from each other along the direction;
a filter disposed to receive an air from the inlet and configured to perform a first deodorization on the air and provide a filtered air, the filter comprising two sidewalls that adjoin to the first sidewall and the second sidewall of the housing;
a fan disposed between the filter and the outlet and having a first region and a second region that are disposed at opposite sides of the fan;

an ion generator disposed between the filter and the outlet and configured to perform a second deodorization on the filtered air from the filter;

a first holder disposed in the housing and having a first region and a second region that are in contact with opposite sides of the fan, respectively;

a second holder disposed in the housing and configured to be in contact with the ion generator; and a light emitter in the housing and configured to emit light toward the filtered air, the light emitter disposed between the filter and the fan;

a wall extending from the first region of the first holder to one side of the housing and configured to guide the filtered air to flow toward the ion generator, and wherein the ion generator is configured to generate ions that react with the filtered air while the filtered air passes through a region disposed between the wall and the outlet, and wherein the filter, the fan, and the ion generator are disposed along a first straight direction and the light emitter extends along a second direction perpendicular to the first straight direction.

16. The deodorization apparatus of claim 15, wherein the wall adjoins an upper region of the housing.

17. The deodorization apparatus of claim 15, wherein the wall is disposed on one side of the fan.

18. The deodorization apparatus of claim 15, wherein the light emitter includes a plurality of light emitting sources that is configured to emit light having different wavelengths from each other.

19. The deodorization apparatus of claim 15, wherein the light emitter is configured to emit the light toward the region.

\*    \*    \*    \*    \*